(12) United States Patent
Garuti

(10) Patent No.: US 6,416,791 B1
(45) Date of Patent: Jul. 9, 2002

(54) ALIMENTARY INTEGRATOR

(76) Inventor: Eliseo Garuti, 33312 Valdedios-Villaviciosa, Asturias (ES)

( * ) Notice: Subject to any disclaimer, the term of this patent is extended or adjusted under 35 U.S.C. 154(b) by 0 days.

(21) Appl. No.: 09/672,720

(22) Filed: Sep. 28, 2000

Related U.S. Application Data

(63) Continuation-in-part of application No. 09/400,328, filed on Sep. 21, 1999, now abandoned.

(51) Int. Cl.$^7$ .................. A61K 33/00; A61K 31/34; A61K 31/70
(52) U.S. Cl. .................. 424/722; 424/717; 426/72; 514/23; 514/474; 127/29; 536/1.11; 549/315
(58) Field of Search .............. 514/23, 25, 474, 514/724, 738; 424/715, 717, 722; 426/72; 536/1.11; 127/29; 549/315

(56) References Cited

U.S. PATENT DOCUMENTS

| | | | | |
|---|---|---|---|---|
| 4,760,138 A | * | 7/1988 | So et al. ............... | 536/102 |
| 5,424,074 A | * | 6/1995 | Koli et al. ............. | 424/464 |
| 5,626,883 A | * | 5/1997 | Paul ..................... | 424/605 |
| 6,051,236 A | * | 4/2000 | Portman ................ | 424/195.1 |

OTHER PUBLICATIONS

Varmus et al. 1993 Genes and the *Biology of Cancer*, Scientific American Library, 1993, No.

Von Euler H. et al., 1945, *Cancer biochemistry–La biochimica dei tumori*, Cap. II. Pp. 78–84. Einaudi–Torino, 1945, No.

Dallaporta B. et al., 1998, Potassium leakage during the apoptotic degradation phase, *The Journal of Immunology*, 1998, pp. 5605–5615), Yes.

Hughes F. et al., 1997, Intracellular K+ Suppresses the Activation of Apoptosis in Lymphocytes, *The Journal of Biological Chemistry*, vol. 272, n. 48, 1997, pp. 30567–30576, Yes.

Bortner C. et al., 1997, Efflux in the Activation of Apoptosis, *The Journal of Biological Chemistry*, vol. 272, n. 51, 1997, pp. 32436–32442, Yes.

Moran et al., 1994, *Biochemistry*, $2^{nd}$ edition Prentice Hall, Inc. 1994, No.

\* cited by examiner

*Primary Examiner*—Jose' G. Dees
*Assistant Examiner*—Frank Choi
(74) *Attorney, Agent, or Firm*—McGlew and Tuttle, P.C.

(57) ABSTRACT

The invention relates to an alimentary integrator constitued by a compound of potassium bicarbonate ($KHCO_3$) and an anti-oxidant agent that comprises D ribose ($C_6H_{10}O_5$) and that can comprise ascorbic acid L ($C_6H_8O_6$).

13 Claims, 11 Drawing Sheets

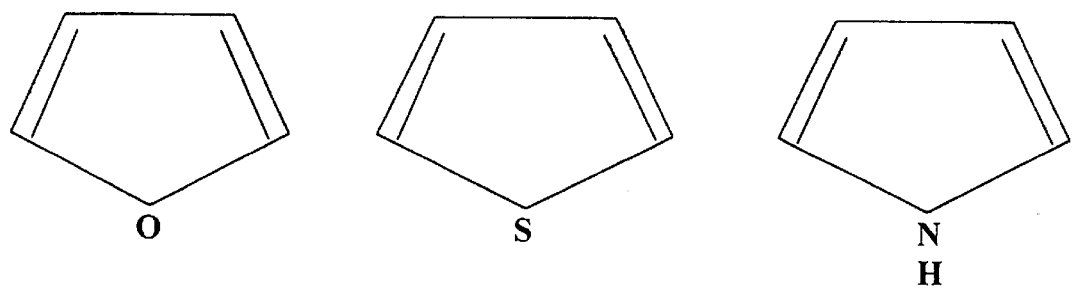
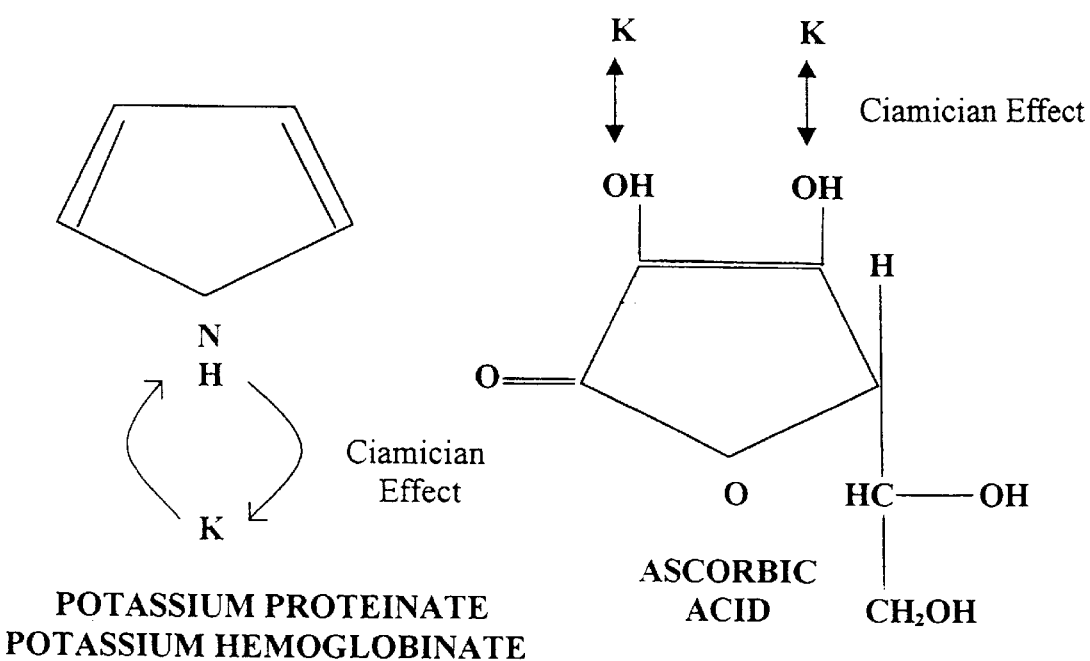
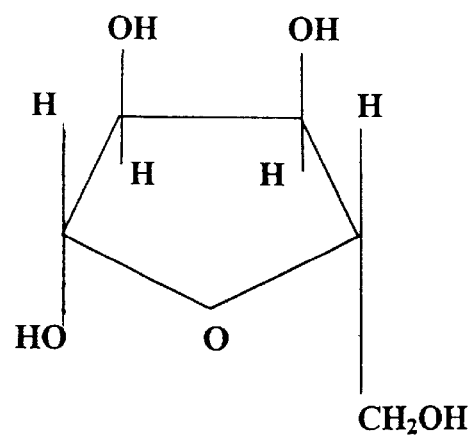
Fig. 1

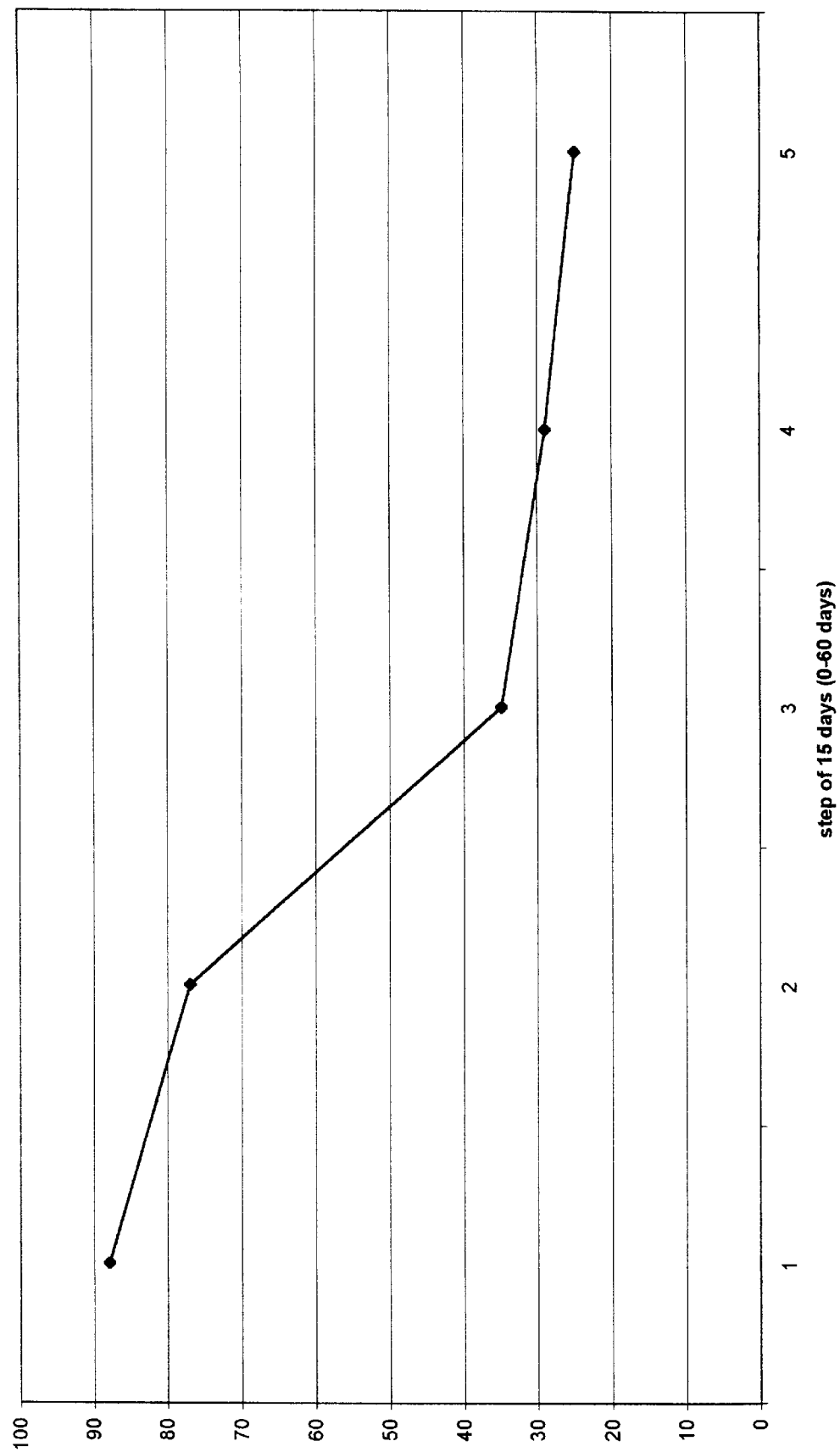

ALIMENTARY INTEGRATOR

CROSS-REFERENCE TO RELATED APPLICATION

This is a continuation-in-part of co-pending application Ser. No. 09/400,328 file Sep. 21, 1999, now abandoned.

FIELD OF THE INVENTION

The present invention relates to an alimentary integrator and a method which are particularly useful in treating or preventing diseases or conditions involving; degenerative forms, weakening of the immune system and stepped-up organic deterioration.

BACKGROUND OF THE INVENTION

It is a well-known fact that atmospheric and environmental (including electromagnetic) pollution, radiation in general, an irregular diet (with an excess of peroxidated food fats) and food alterations themselves (preservatives, genetically modified substances, etc.), cigarette smoke, prolonged emotional stress and immune and inflammatory reactions are a continual source of free radicals which cause damage to the organism on the cellular level by way of chemical oxidizations of lipids and proteins (oxidated stress). The same angiogenesis, triggering off a hyperoxygenation of the new cytoplasmatic capillary vessels is itself a source of oxidizing stress. The general effects thus produced in the organism are mainly the following: a weakening of the immune system; a stepped-up physiological organic deterioration, and the production of degenerative forms.

In this way biological, physical and chemical alterations are formed that can cause damage to the cellular membrane and to the DNA.

In fact, in the presence of oxidizing stress, the $NA^+$—$K^+$ pump does not perform its task correctly and there occurs an imbalance of the four fundamental cations which are needed to maintain cellular functioning, namely sodium, potassium, calcium and magnesium.

Especially in the presence of degenerative diseases and in particular neoplastic forms. Sodium $NA^+$ (a prevalent cation in extracellular fluids) tends to substitute potassium $K^+$ inside the cell with a resulting serious imbalance find alteration of the NA—K pump.

It is known by Varmus et al. ("Genes and the Biology of Cancer"—Scientific American Library, 1993) that the production of degenerative forms is bound to an anomalous cellular behaviour deriving from oxidizing stress that can originate a monotonic polymerization, that is to say uncontrolled proliferation and growth. Although there are different types of degenerative pathologies, the processes that determine them look like the same.

In fact, the oxiding stress causes an imbalance in the concentration of $K^+$ and $Na^+$ cations and a malfunctioning of the $Na^+$—$Ka^+$ pump and consequent heavy loss of electrolytes not only in the Na—K pump but also in the concentration of the other electrolytes, i.e., calcium and magnesium. Said features were pointed out by Von Euler H. et al. ("Cancer biochemistry—La biochimica dei tumori." Cap.II. pp. 78–84 Einaudi -Torino, 1945).

The importance of potassium in the regulation of cellular metabolism was pointed out by Dallaporta B. et al. ("Potassium leakage during the apoptotic degradation phase". The Journal of Immunology, 1998, pp. 5605–5615), by Hughes F. et al. ("Intracellular $K^+$ Suppresses the Activation of Apoptosis in Lymphocytes".—The Journal of Biological Chemistry, Vol. 272, n. 48, 1997, pp. 30567–30576) and by Bortner C. et al. ("Efflux in the Activation of Apoptosis"—The Journal of Biological Chemistry, Vol. 272, n. 51, 1997, pp. 32436–32442) relating to the cellular apoptosis and by Moran et al. ("Biochemistry" 2nd edition, Prentice Hall, Inc., 1994) relating the rule of co-factor of potassium in the enzymatic catalysis.

U.S. Pat. No. 4,760,138 to So et al. deals with carbonating agents for beverages and uses the calcium ion for medicinal or nutritive supplementation of calcium in the diet.

U.S. Pat. No. 5,424,074 to Koli et al. recognizes the need for potassium in the body, but offsets its deficiency and attendant adverse retention of sodium by a composition combining a magnesium compound with a potassium compound and both an effervescing agent and a neutralizing agent, desirably having ingredients that mask the objectionable taste of potassium.

U.S. Pat. No. 5,626,883 to Paul recognizes the need for ascorbic acid in the body and avoids the initial transitory suppression of human natural killer cells which occurs when ascorbic acid is administered alone, by combining a water soluble form thereof, such as ascorbic acid, niacinamide ascorbate or a metal ion salt of ascorbic acid, with a fat soluble ascorbyl ester and desirably also an ascorbic acid metabolite or precursor.

The aforesaid compound are composed from a very great number of components and their preparation isn't very simple.

SUMMARY AND OBJECTS OF THE INVENTION

A first aspect of the invention concerns an alimentary integrator which comprises a compound formed from potassium bicarbonate and an anti-oxidant agent comprising ribose, or ribose and I-ascorbic acid.

In one embodiment, the integrator comprises potassium ribosate formed from potassium bicarbonate and ribose, such as two, three, or four parts by weight of potassium bicarbonate and one part by weight of ribose.

The two components of the potassium ribosate may be in associated corresponding single dosage form, combinable at the time of use for obtaining an extemporary solution of the integrator.

In an alternative embodiment, the integrator comprises potassium ribose ascorbate formed from potassium bicarbonate, ribose and I-ascorbic acid, such as two or four parts by weight of potassium bicarbonate, one part by weight of I-ascorbic acid and an amount of ribose corresponding to 0.1–10%, especially about 2%, by weight of the sum of the weights of the potassium bicarbonate and I-ascorbic acid. The three components of the potassium ribose ascorbate may be in associated corresponding single dosage form, combinable at the time of use for obtaining an extemporary solution of the integrator.

Specifically, the alimentary integrator comprises a compound selected from potassium ribosate and potassium ribose ascorbate, such as wherein the potassium ribosate is formed from two to four parts by weight of potassium bicarbonate and one part by weight of ribose, or wherein the potassium ribose ascorbate is formed from two or four parts by weight of potassium bicarbonate, one part by weight of I-ascorbic acid and an amount of ribose corresponding to 0.1–10% by weight of the sum of the weights of the potassium bicarbonate and I-ascorbic acid. The two components of the potassium ribosate, or the three components of the potassium ribose ascorbate, as the case may be, may be in associated corresponding single dosage form, combinable at the time of use for obtaining an extemporary solution of the integrator.

A second aspect of the invention concerns a method of treating or preventing a potassium deficiency based disease or condition in a subject involving weakening of the immune system, stepped-up physiological organic deterioration or the production of cellular degenerative forms, by administering to the subject an effective amount of an alimentary integrator which comprises a compound formed from potassium bicarbonate and an anti-oxidant agent comprising ribose, or ribose and I-ascorbic acid. In particular, the integrator comprises potassium ribosate formed from potassium bicarbonate and ribose, or potassium ribose ascorbate formed from potassium bicarbonate, ribose and I-ascorbic acid.

Specifically, the method comprises administering to the subject an effective amount of an alimentary integrator which comprises a compound selected from potassium ribosate and potassium ribose ascorbate, such as wherein the potassium ribosate is formed from two to four parts by weight of potassium bicarbonate and one.part by weight of ribose, or the potassium ribose ascorbate is formed from two or four part s by weight of potassium bicarbonate, one part by weight of I-ascorbic acid and an amount of ribose corresponding to 0.1–10% by weight of the sum of the weights of the potassium bicarbonate and I-ascorbic acid.

The two components of the potassium ribosate, or the three components of the potassium ribose ascorbate, as the case may be, may be in associated corresponding single dosage form, combinable at the time of use for obtaining an extemporary solution of the integrator.

The alimentary integrator and method of use of the invention serve to supply potassium to the body on a cellular level for treating or preventing an inherently potassium deficiency based disease or condition involving weakening of the immune system, stepped-up physiological organic deterioration or production of cellular degenartive forms. Per the invention, potassium ribosate is usable instead of potassium ribose ascorbate such as where the person treated is allergic to ascorbic acid.

An aim of the present invention is to eliminate the above mentioned drawbacks by providing an alimentary integrator having the characteristics of the claims.

Among the advantages of the present invention is that the integrator is a very powerful anti-oxidizing agent that reduces the effect of free radicals; that it strengthens the activity of the immune system maintaining or revitalizing the concentration of intracellular potassium to the required levels; that it ties together the functional characteristics of its components giving rise to results surprisingly better in respect to the components singularly used, with a synergistic action of the components: that it is completely atoxic (at prescribed doses); that it can be used over a long period of time; that it has a very simple posology. A further advantage is that the integrator is formed from only two components in the embodiment of potassium ribosate, and from only three components in the embodiment of ribose ascorbate.

The present invention points out that potassium may be regarded as a "co-factor," i.e., a substance upon which the catalytic activity of many enzymes depends, potassium being a fundamental element for proteic functions and for regulating cellular activity. In this regard, it is to be pointed out that it has been long known that after an oxidizing stress the final effect of cellular deterioration is a loss of intracellular potassium with the inlet of extracellular potassium into the cytoplasm, and consequent heavy loss of electrolytes not only in the Na-K pump but also in the concentration of the other electrolytes, i.e., calcium and magnesium. The loss of potassium is due to the opening of the pyrrolic rings of proteins, of cytoplasmatic enzymes and of membrane proteins, to which the potassium bonds itself reversibly for carrying out its function. As a result of the above, the cells cannot function in regular manner. Upon cytoplasmatic damage to the pyrrole proteic groups, the consequent lack of potassium not only is accompanied by hypoparathyroidism, vitamin deficiency, nephrosis, renal failure, etc., but also signifies a proliferation of cellular deterioration. In other words, potassium is a critical "factor" for regulating cellular activity.

Per the invention, ribose (potassium ribosate) or combined ribose-ascorbic acid (potassium ribose ascorbate) in the instant alimentary integrator possess not only the known anti-oxidant action of the individual components (ribose and ascorbic acid), but also a heretofore unknown function as potassium "carrier" in the cytoplasm. The instant alimentary integrator thus effects transport of potassium into the cytoplasm of a cell affected by cellular deterioration, damage to pyrrolic groups of angiogenesis phenomena.

This potassium transport is attained by means of the associated ribose (potassium ribosate) or combined ribose-ascorbic acid (potassium ribose ascorbate) of the instant alimentary integrator due to the biochemical-physical features of the ribose and combined ribose-ascorbic acid components. Of course, the molecules of these two components have a cyclic structure of the furanosic type, enabling them to be substituted for damaged protein pyrrolic groups and bind their potassium to such protein, e.g., by salifying the OH groups of these molecules, owing to their particular affinities to the pyrrole NH group, the pyrrole group also being salified by the attendant potassium.

BRIEF DESCRIPTION OF THE DRAWINGS

Further objects, features and advantages of the invention will be apparent upon the consideration of the following detailed description, also taken in conjunction with the accompanying drawings, wherein:

FIG. 1 shows structural formulas of molecules interesting the present invention:

FIGS. 8, 9, 10 and 11 are graphs showing the mean change in physiological parameters of patients treated with an alimentary integrator according to the present invention.

DETAILED DESCRIPTION OF THE PREFERRED EMBODIMENTS

Figure 2:
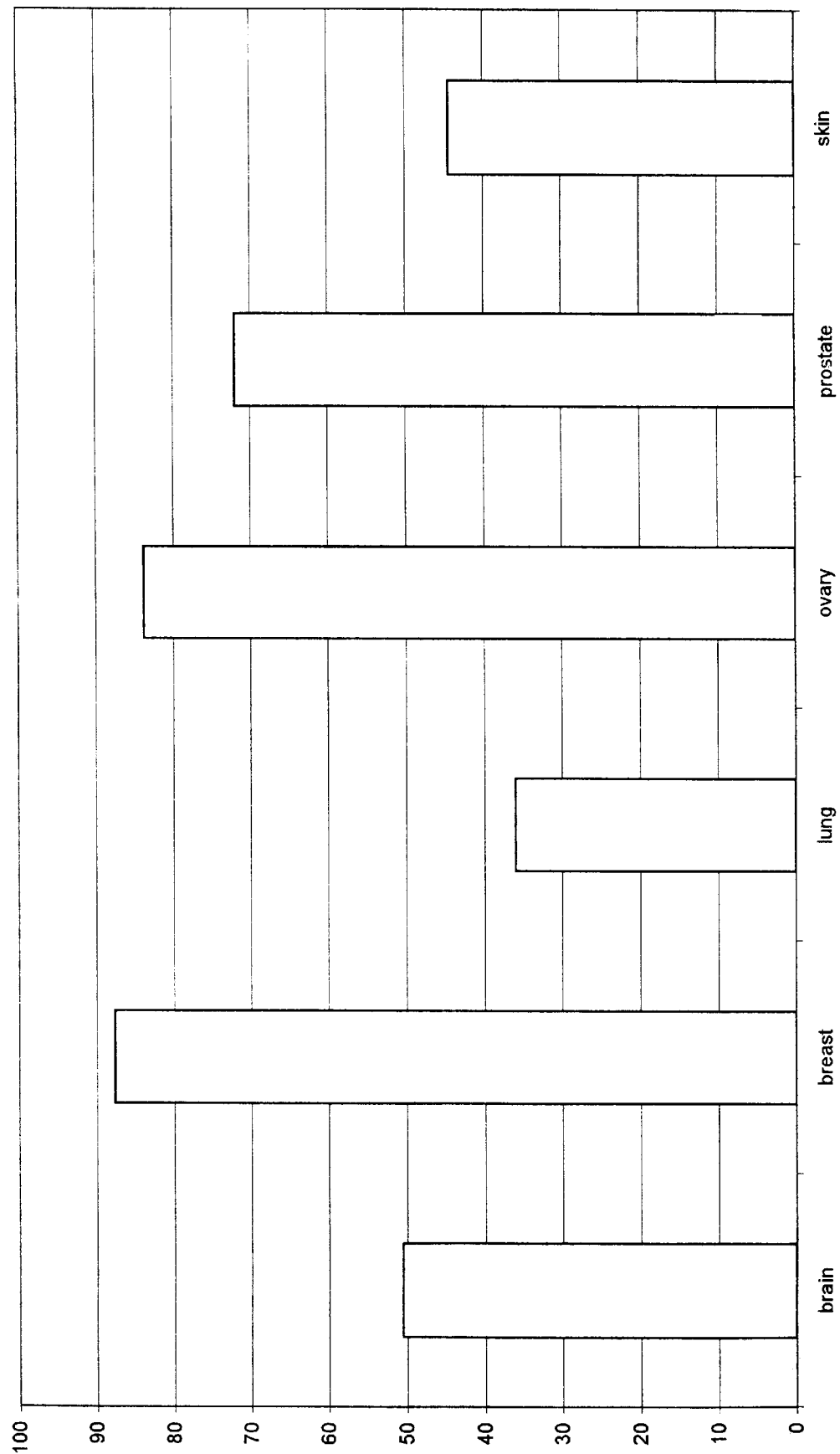
FIG. 2 is a graph showing the survival percentage after five years among patients treated with an alimentary integrator according to the present invention.

The alimentary integrator of the present invention is constitued by a compound of potassium bicarbonate (KHC03) and an anti-oxidant agent that comprises D ribose (C5 H10 O5) and that can also comprise ascorbic acid L (C6 H8 O6).

In a possible embodiment, the integrator is constitued by a salt derived from ascorbic acid L, and is obtained by uniting potassium bicarbonate, ascorbic acid 1, and D ribose in the purest crystallized form. The compound thus obtained, soluble in water, takes the name of potassium ribose ascorbate.

Ascorbic acid salifies easily with alkali bicarbonates dissolved in cold distilled water and with warm alkaline earth carbonates at a temperature of 45–50° C., and working out of CO2. By cold evaporation, under high vacuum, crystallized salts (ascorbates) are obtained.

Potassium ribose ascorbate is a pure microcrystalline easily water-soluble white salt and somewhat unstable due to its easy oxidizability. It is secured through the salification of ascorbic acid L and D ribose in cold water solution with potassium bicarbonate. Its action does not produce any toxicity (given the stated dosages) and can be used for a long time. Biologically it follows the pattern of ascorbic acid. Potassium ribose ascorbate, as an ascorbic acid derivate, can take on two isomeric configurations: the oenolic form and the furanoid form; when in solution it assume the latter form.

Potassium ribose ascorbate, as expressed above, is a very powerful anti-oxidizing agent, completely atoxic that can be used over a long period of time (at prescribed doses), and acts in a way that reduces the effect of free radicals, strengthening the activity of the immune system and maintaining or revitalizing the concentration of intracellular potassium to the required levels. It is therefore a most valid alimentary integrator and a very powerful cellular anti-oxidizer which ties together the functional characteristics of ascorbic acid L and of potassium, manifesting itself as more active (synergistic) than the two constituents separatety taken. Moreover, the presence of D ribose, for its characteristics of a molecule structurally present in the intimate architecture of the cell, makes the compound more effective, i.e., amplifies its effect.

Blood haemoglobin contains pyrrolic rings in its molecule; equally pyrrolederivates must be considered many fundamental amino acids. Also of note is the fact that black pigments, skin, hair, moles or birth-marks, etc. are closely related to pyrrole black spots, which allows the assumption that said pigments are oxidized compounds and polycondensed compounds having a pyrrolic stucture.

Referring also to FIG. 1, pyrrole, thiophene and furan are similar to each other; in the formation of their compounds they follow Angeli's rule of analogies. It is therefore reasonable to assume that during the biological synthesis process of protein derivatives from such compounds there may occur analogous chemical and physiological reactions and that under particular conditions a pyrrolic group may be replaced by a similar thiophenic or furanoid group.

It is important to note that the hydrogen present in the pyrrolic structure can be easily replaced by the potassium cation but not by the sodium cation (the Ciamician effect), regardless of the physical and chemical affinity between these two.

Both potassium haemoglobinate and potassium proteinate contain pyrrolic structures which can be salified with KHC03; the potassium ribose ascorbate contains in its molecule a furanosic group which by analogy may replace one of the pyrrolic groups of potassium haemoglobinate and proteinate.

This is of the utmost importance because at the beginning of a degenerative process, particularly of neoplastic type, the pyrrolic groups are inactive and it is quite likely that the starting point of a degenerative disease is the peptide molecule containing pyrrolic groups at the RNA level. It is assumed that the opening of the pyrrolic molecule (the Ciamician effect) may give rise to a triggering off of RNA polymerization, this being the beginning of the biological phase of a neoplasia.

Therefore potassium ribose ascorbate, in reactivating the pyrrolic group, restores the structuring phenomena of the cellular auto-synthesis to the required physiological normality.

Besides, since salification is a reversible process, potassium ribose ascorbate, carried by haemoglobin and introduced into the cell, re-establishes the equilibrium amongst the intermolecular- forces of the peptide groups which are present inside the cell membrane and brings back (or maintains) the required levels of the intracellular potassium concentration.

Finally, ascorbate acid L residing in potassium ribose ascorbate is fully capable of carrying out its functions, protecting above all the cell from the effects of free radicals, precisely by virtue of its anti-oxidizing characteristics, while D ribose, as previously pointed out, amplifies the effect of the compound.

Potassium ribose ascorbate is especially active against degenerative disease since, as explained earlier, when confronted by a degenerative process, it corrects the process of cellular metabolism by inhibiting its progress and giving it back the equilibrium of its functions with satisfactory results.

It emerges from stoichiometric calculations that the proportion between potassium bicarbonate and ascorbic acid L must be of a 2—1 relation. In particular conditions, it is possible to double the amount of potassium bicarbonate, determining a 4—1 relation.

Regarding the storage and the dosage, the potassium ribose ascorbate must be protected from humidity and the sun's rays and preserved separately in bags, phials or other suitable containers for preparing an extemporary solution of very pure ascorbic acid L, D ribose and bicarbonate of potassium according to the proportions deriving from the experimental tests and of which is described an example.

Each extemporary preparation comprises a bag or a phial of ascorbic acid L containing a dose of same, a bag or a phial of potassium bicarbonate containing two doses of same and a bag or a phial of D ribose containing an amount between 0.1% and 10%, preferably 2%, of the inclusive dosage of potassium ascorbate. In the bag the contents are crystallized, in the phial the contents are in solution of distilled water.

In the administering of potassium ribose ascorbate as a therapy against degenerative diseases, the contents of a dose of ascorbic acid L, D ribose,(2%) and two doses of potassium bicarbonate can be blended in order to obtain the cold extemporary solution of potassium ribose ascorbate to be administered, for example, three times a day.

Experimentally, it is established that the general course of action above described may undergo variations due to particular physiopathological conditions, according to medical evaluation, for instance, by doubling the potassium bicarbonate dosage (determining the 4-1 relation between KHC03 and C6 H8 06 above mentioned) or by reducing the administration of the medication to twice per day; at any rate, the maximum dosage of potassium ribose ascorbate should not exceed 3 g daily.

At the preventive level, potassium ribose ascorbate can be used at the same dosages of therapy but is can be administered only once a day, on alternate days. For children, maintaining the same dosages, the preventive administration changes with the age.

In another possible embodiment, the compound of the present invention is a salt derived from D ribose and it is obtained by uniting potassium bicarbonate and D ribose in the purest crystallized form. The compound thus obtained, soluble in water, takes the name of potassium ribosate.

It is particularly effective in degenerative forms for people (subjects) allergic to ascorbic acid L and to ascorbate (in particular to potassium ascorbate).

It is known that ascorbic acid L and D ribose are molecules of similar structure, and belong with the same functional group in which the hydroxyl O—H in the reaction affected in the potassium ribose ascorbate formation is substituted by the O—K group.

In this way, it can be deemed as a substratum or the precursor of another in biochemical reactions.

Therefore, in pathologic situations of allergy to ascorbic acid L, D ribose is a fundamental substitute, with similar functional characteristics.

Ribose salifies easily with alkali bicarbonates dissolved in cold distilled water and with warm alkaline earth carbonates at a temperature of 45–50° C., and working out of C02, for its structural and functional characteristics similar to ascorbic acid. By cold evaporation, under high vacuum, crystallized salts (ribosates) are obtained.

Potassium ribosate is a pure microcrystalline easily water-soluble white salt and somewhat unstable due to its easy oxidizability. It is secured through the salification of D ribose in cold water solution with potassium bicarbonate. Its action does not produce any toxicity (given the stated dosages) and can be used for a long time. Biologically it follows the pattern of ascorbic acid.

Potassium ribosate. as an ascorbic acid precursor, it can take on two isomeric configurations: the oenolic form and the furanoid form; when in solution it assumes the latter form.

Also potassium ribosate, similarly to potassium ribose ascorbate, is a very powerful anti-oxidizing agent, completely atoxic that can be used over a long period of time(at prescribed doses), acts in a way that reduces the effect of free radicals, strengthening the activity of the immune system and maintaining or revitalizing the concentration of intracellular potassium to the required levels. It is therefore a most valid alimentary integrator and a very powerful cellular anti-oxidizer which ties together the functional characteristics of D ribose and of potassium, manifesting itself as more active (synergistic) than the two constituents separately taken.

As said about potassium ribose ascorbate, blood haemoglobin contains pyrrolic rings in its molecule; equally pyrrole derivates must be considered many fundamental amino acids. Also of note is the fact that black pigments, skin, hair, moles or birth-marks, etc are closely related to pyrrole black spots, which allows the assumption that said pigments are oxidized compounds and polycondensed compounds having a pyrrolie structure.

Referring also to FIG. 1, pyrrole, thiophene and furan are similar to each other; in the formation of their compounds they follow Angeli's rule of analogies. It is therefore reasonable to assume that during the biological synthesis process of protein derivatives from such compounds there may occur analogous chemical and physiological reactions and that under particular conditions a pyrrolic group may be replaced by a similar thiophenic or furanoid group.

It is important to note that the hydrogen present in the pyrrolic structure can be easily replaced by the potassium cation but not by the sodium cation (the Ciamician effect), regardless of the physical and chemical affinity between these two.

Both potassium haemoglobinate and potassium proteinate contain pyrrolic structures which can be salified with KHC03; the potassium ribose ascorbate contains in its molecule a furanosic group which by analogy may replace one of the pyrrolic groups of potassium haemoglobirtate and proteinate.

This is of the utmost importance because at the beginning of a degenerative process, particularly of neoplastic type, the pyrrolic groups are inactive and it is quite likely that the starting point of a degenerative disease is the peptide molecule containing pyrrolic groups at the RNA level. It is assumed that the opening of the pyrrolic molecule (the Ciamician effect) may give rise to a triggering off of RNA polymerization, this being the beginning of the biological phase of a neoplasia.

Therefore potassium ribosate, in reactivating the pyrrolic group, restores the structuring phenomena of the cellular auto-synthesis to the required physiological normality.

Besides, since salification is a reversible process, potassium ribosate, carried by haemoglobin and introduced into the cell, re-establishes the equilibrium amongst the intermolecular forces of the peptide groups which are present inside the cell membrane and brings back (or maintains) the required levels of the intracellular potassium concentration.

Finally, the compound potassium ribosate protects the cell tom the effects of free radicals, precisely by virtue of its anti-oxidizing characteristics.

Potassium ribosate is especially active against degenerative disease since, as explained earlier, when confronted by a degenerative process, it corrects the process of cellular metabolism by inhibiting its progress and giving it back the equilibrium of its functions with satisfactory results.

It emerges from stoichiometric calculations that the proportion between potassium bicarbonate and ribose must be of a 2—1 relation, but it is possible a 3—1 relation. Regarding the storage and the dosage, the compound of potassium ribosate must be protected from humidity and the sun's rays and preserved separately in bags, phial, or other suitable containers for preparing an extemporary solution of very pure D ribose and bicarbonate of potassium according to the following preferable proportions The proportions are attained with the use of a bag or a phial of potassium bicarbonate containing two doses of same and a bag or a phial of D ribose containing a dose of same. It is possible to use three doses of potassium bicarbonate and a dose of D ribose.

In the administering of potassium ribosate as a therapy against degenerative diseases, the contents of a dose of ribose and two doses of potassium bicarbonate can he blended in order to obtain the cold extemporary solution of potassium ribosate to be administered, for example, three times a day.

Similarly to potassium ribosate ascorbate, the above described general course of action of potassium ribosate may undergo variations due to particular physiopathological conditions, according to medical evaluation, for instance, doubling the potassium bicarbonate dosage (determining a 4—1 relation between potassium bicarbonate and D ribose) or by reducing the daily administration of the medication; at any rate, the maximum dosage of potassium ribosate should not exceed 2 g daily. At the preventive level and in the administration to children, potassium ribosate can he used similarly to potassium ribose ascorbate.

In FIGS. 2–5 and 8–11 are shown the results of a testing carried out for more than ten years. The testing was carried out on a sample of 30 patients suffering from different types of neoplasia in advanced phase (terminally-ill patients).

The patients were given potassium ribose ascorbate three times a day.

Figure 3:
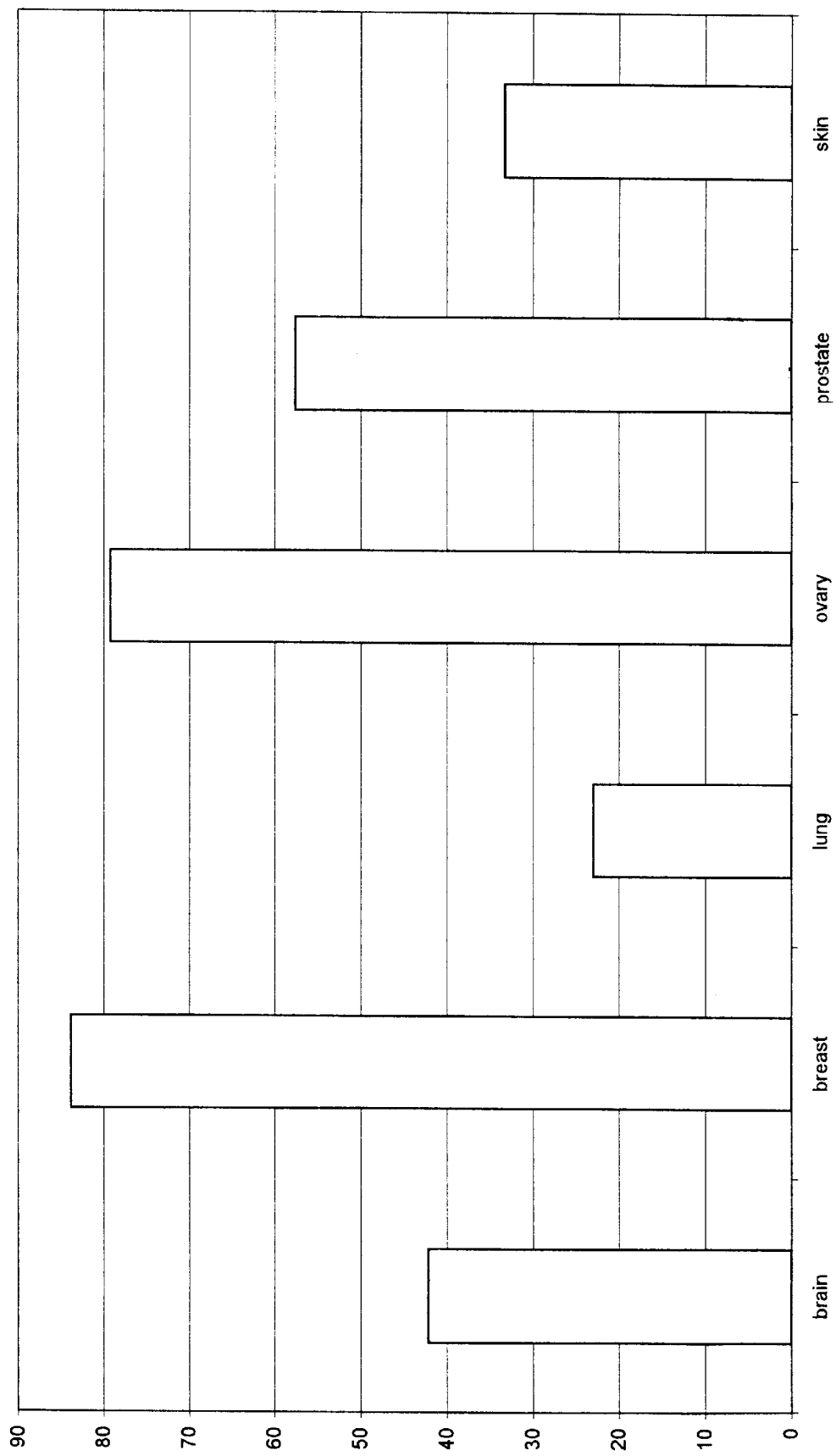
FIG. 3 is a graph showing the survival percentage after ten years among patients treated with an alimentary integrator according to the present invention.
Figure 4:
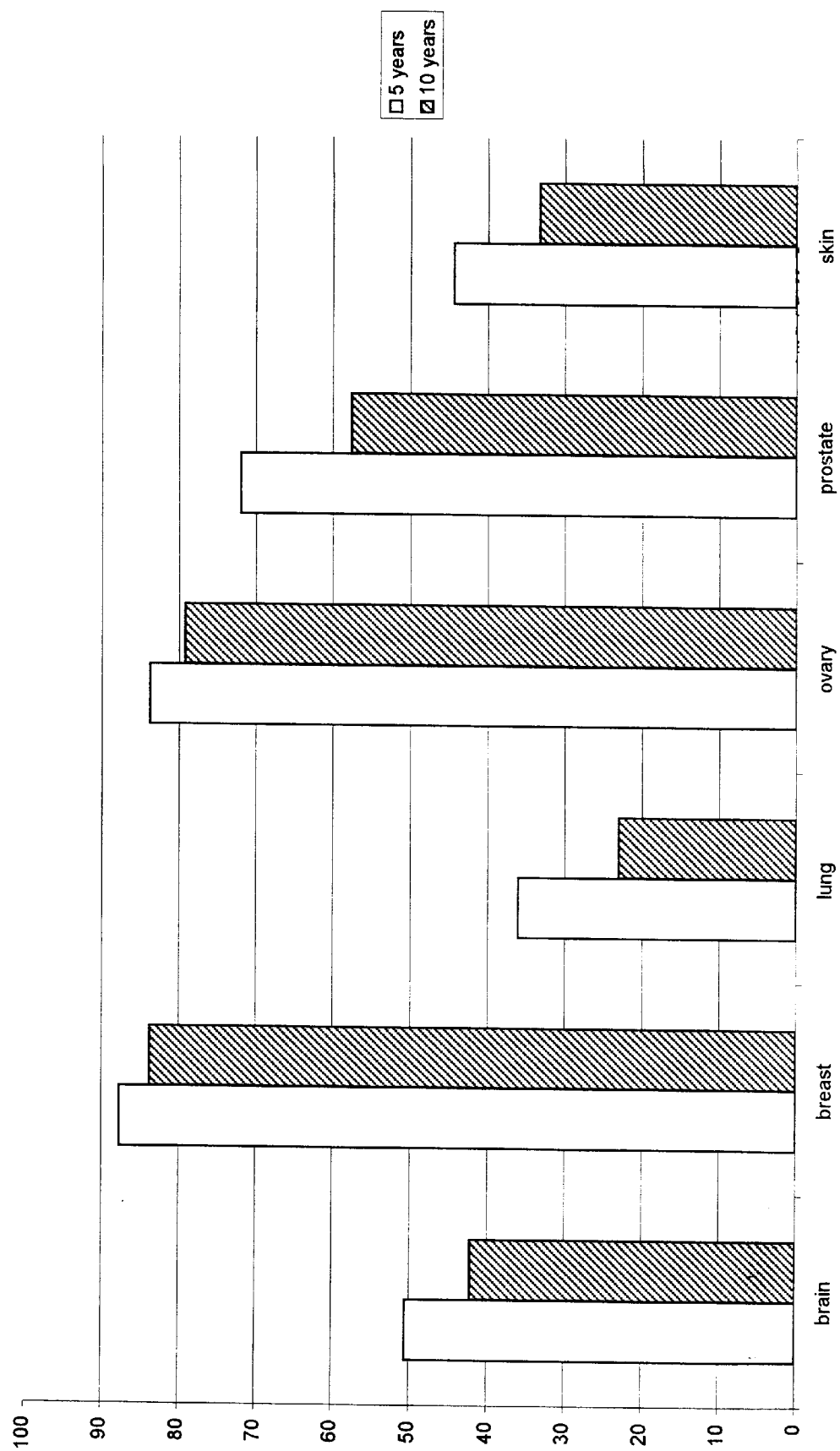
FIG. 4. is a graph showing the survival percentage after five and ten years among patients treated with an alimentary integrator according to the present invention.

The graph of FIG. 2 shows the survival percentage after five years among these patients, while FIG. 3 is a graph showing the survival percentage after ten years, using a different scale in ordinate (In FIG. 1 the ordinate scale has an interval from 0 to 100%; in FIG. 2 the interval is from 0 to 90%) and in FIG. 4 is shown the comparison between said percentages (the ordinate interval is from 0 to 100%, as in FIG. 1) The patients are divided according to the location of the neoplasia: from left to right: brain, breast, lung; ovary, prostate, skin.

It is very manifest that the survival percentages are very high considering the fact that the patients are terminally-ill patients.

Figure 5:
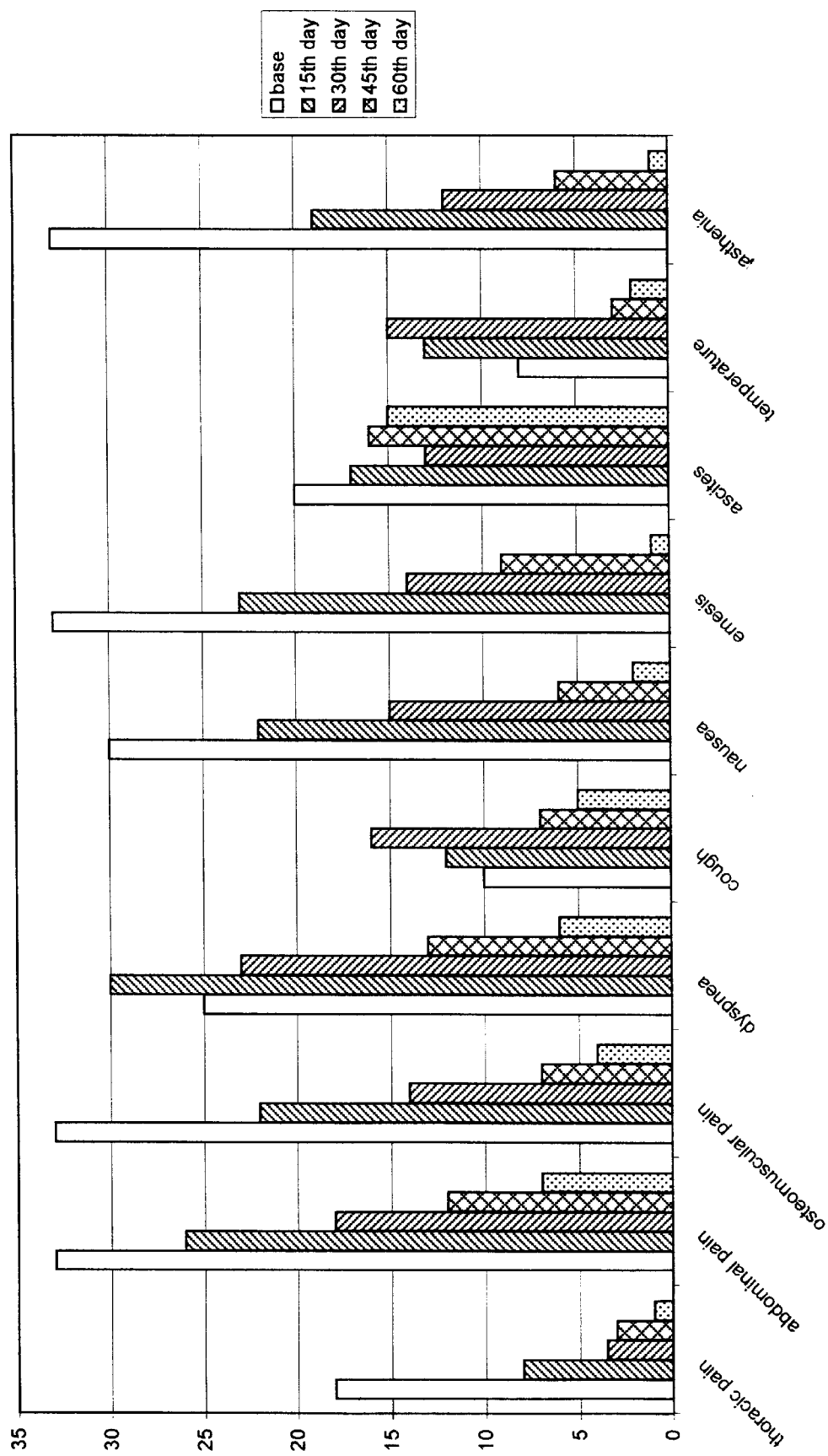
FIG. 5 is a graph showing the change in symptoms among patients treated with an alimentary integrator of the present invention.

The integrator of the present invention not only allows a good survival percentage but also improves the symptoms of the diseases. In FIG. 5 is a graph showing the changes in ten symptoms among the patients above mentioned. On abscissa the graph presents the different symptoms; from left to right thoracic pain, abdominal pain, osteomuscular pain, dyspnea, cough, nausea, emesis, ascites, temperature, asthenia. Every column is composed by five secondary columns which refer to the different time of recording of the data, with 15 days interval, from left to right: base condition (at the beginning of the treatment), at $15^{th}$ day, at $30^{th}$ day, at $45^{th}$ and at $60^{th}$ day The rate utilized as ordinate in the graph is relevant to the intensity (amount) of the symptoms. This rate is a normalized value among the different rates utilized for measuring the ten symptoms (i.e. degrees for the temperature, an objective value for pain, cough, etc). A higher rate means a higher means intensity of the symptom.

It is manifest that all symptoms decreased with the treatment.

The improvement of the condition of patients is manifest also from the change in physiological parameters shown in FIGS. 8, 9, 10 and 11.

Figure 8:
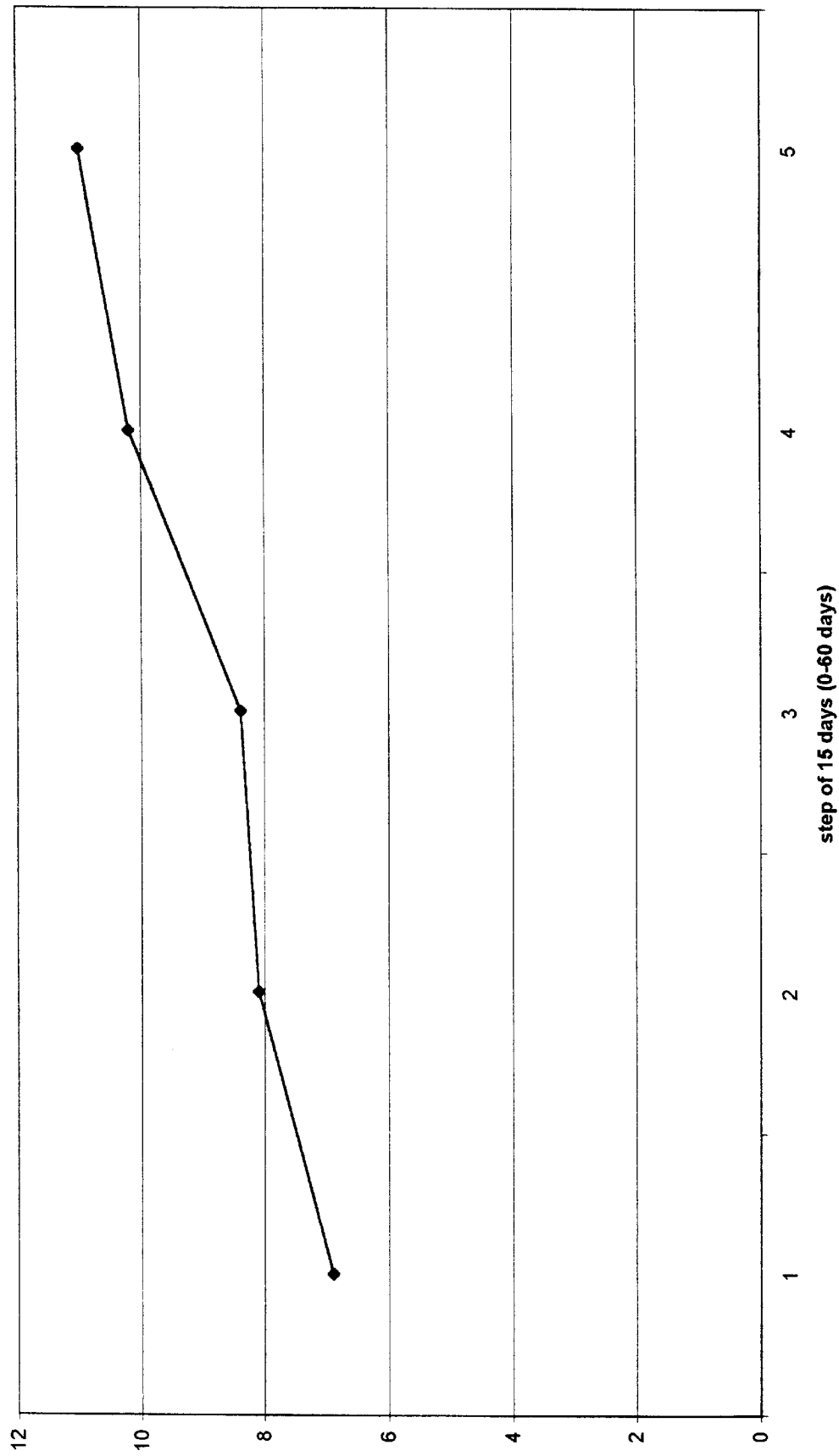
Figure 9:
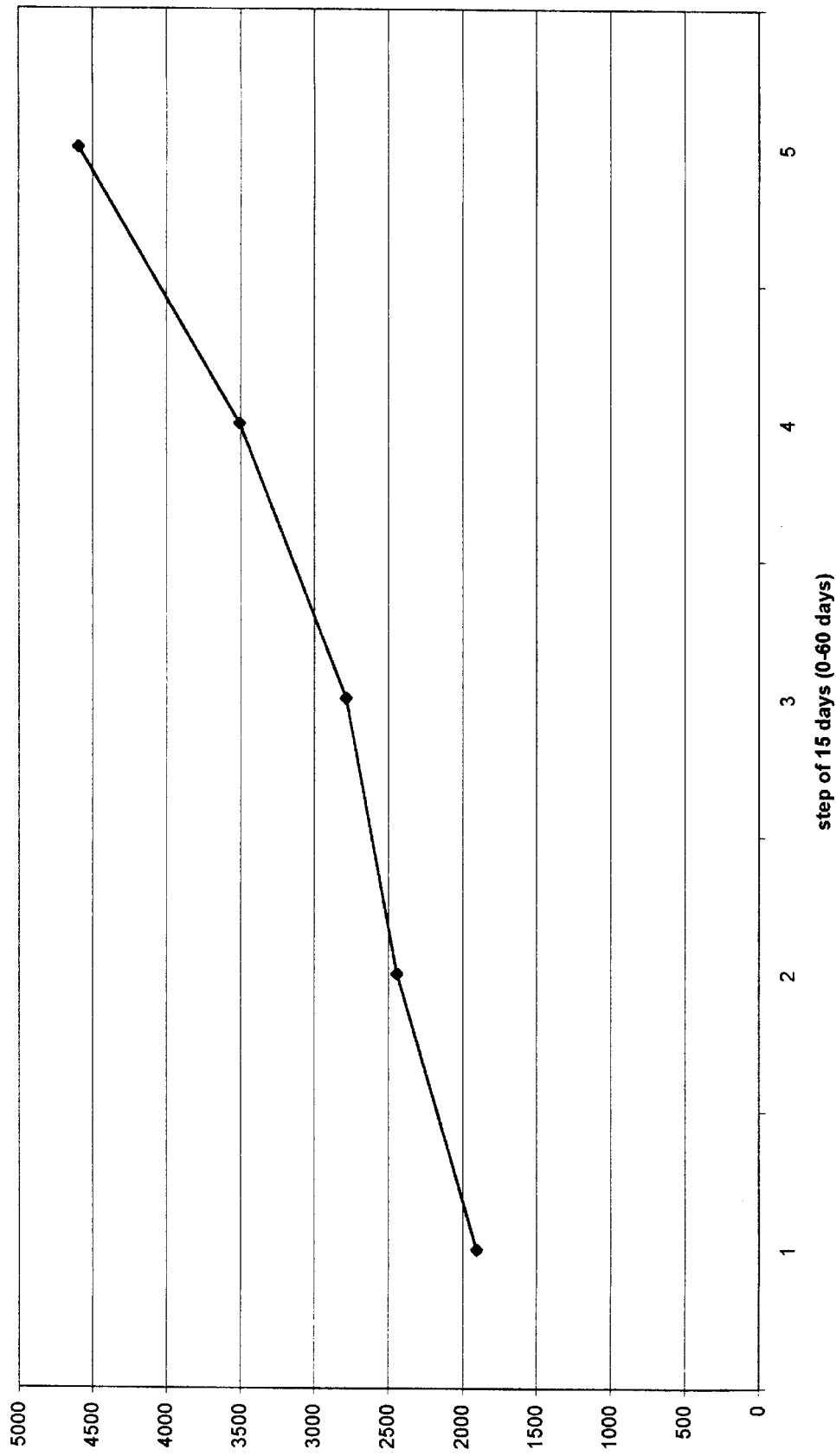
Figure 10:
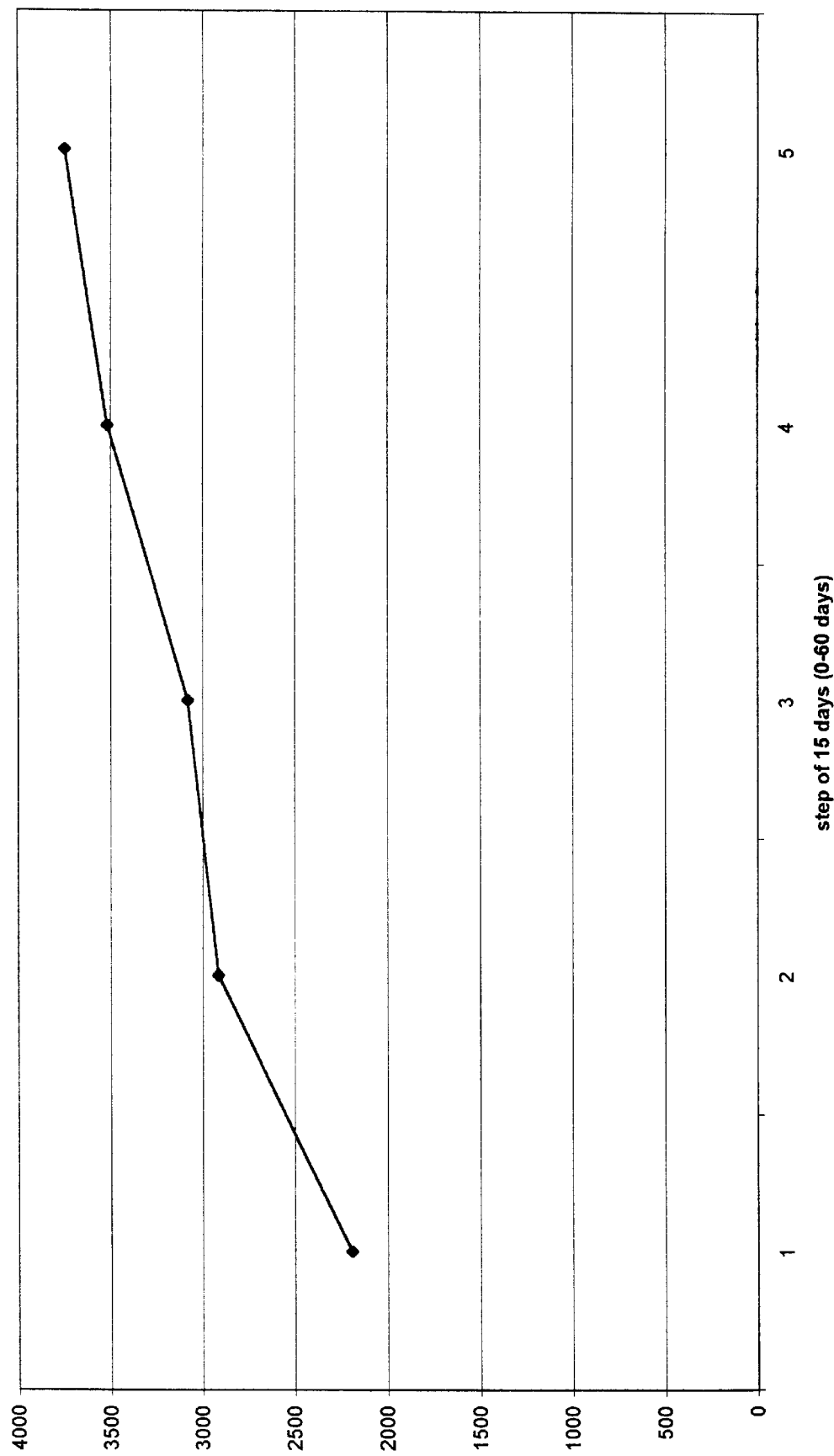

In particular, FIG. 8 is relevant to the mean changes in the hemoglobin rate, in the graph, the abscissa is divided in steps corresponding to 15 days intervals, while the ordinate is expressed in g/dl. FIG. 9 is relevant to the mean changes in the white cells number; in the graph, the abscissa is divided in steps corresponding to 15 days intervals, while the ordinate is expressed in number of cells. FIG. 10 is relevant to the mean changes in the red cells number; in the graph, the abscissa is divided in steps corresponding to 15 days intervals, while the ordinate is expressed in thousands of cells. FIG. 11 is relevant to the mean changes in the erythrosedimentation rate at first hour; in the graph, the abscissa is divided in steps corresponding to 15 days intervals, while the ordinate is expressed in erythrosedimentation rate.

Positively. the graphs of FIGS. 8–10 present increasing rates, while the graph of FIG. 11 presents a decreasing rate.

The choice of the components of the present integrator is very important and decisive because the experimentations have pointed out that only with the two or three components of the compound, exactly taken, it is possible to obtain the objects of the present invention.

As expressed above, ribose (potassium ribosate) or combined ribose-ascorbic acid (potassium ribose ascorbate) in the instant alimentary integrator possess not only the known anti-oxidant action of the individual components (ribose and ascorbic acid), but also a heretofore unknown function as potassium "carrier" in the cytoplasm. The instant alimentary integrator thus effects transport of potassium into the cytoplasm of a cell affected by cellular deterioration, damage to pyrrolic groups or angiogenesis phenomena. This potassium transport is attained by means of the associated ribose (potassium ribosate) or combined ribose-ascorbic acid (potassium ribose ascorbate) of the instant alimentary integrator due to the biochemical physical features of the ribose and combined ribose-ascorbic acid components. Of course, the molecules of these two components have a cyclic structure of the furanosic type, enabling them to be substituted for damaged protein pyrrolic groups and bind their potassium to such protein, e.g., by salifying the OH groups of these molecules, owing to their particular affinities to the pyrrole NH group, the pyrrole group also being salified by the attendant potassium.

The substitution of one or more components of the compound causes an inefficacy of the relevant different compound.

Figure 6:
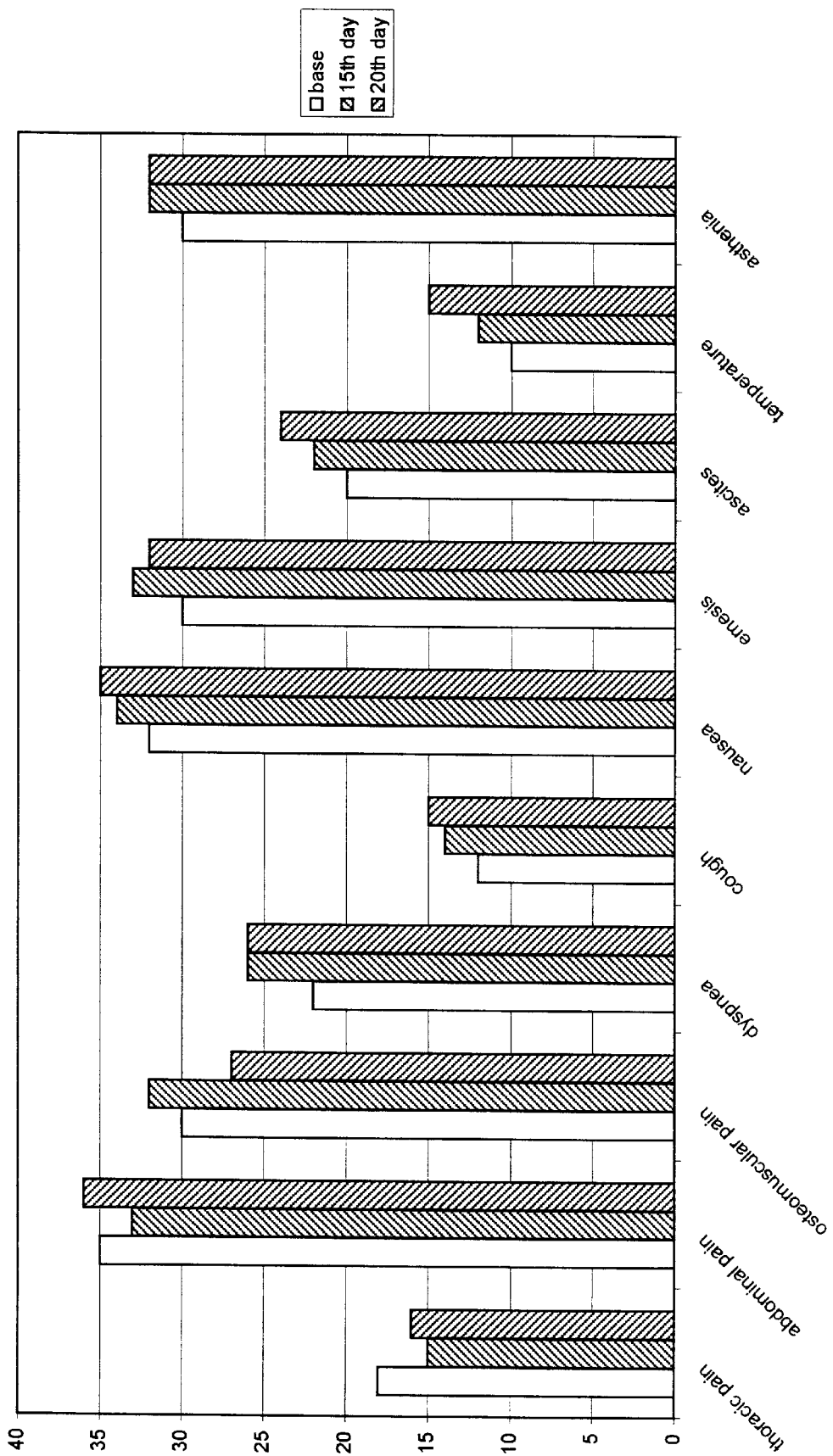
FIG. 6 is a graph showing the change in symptoms among patients treated with a first compound different from the alimentary integrator of the present invention.
Figure 7:
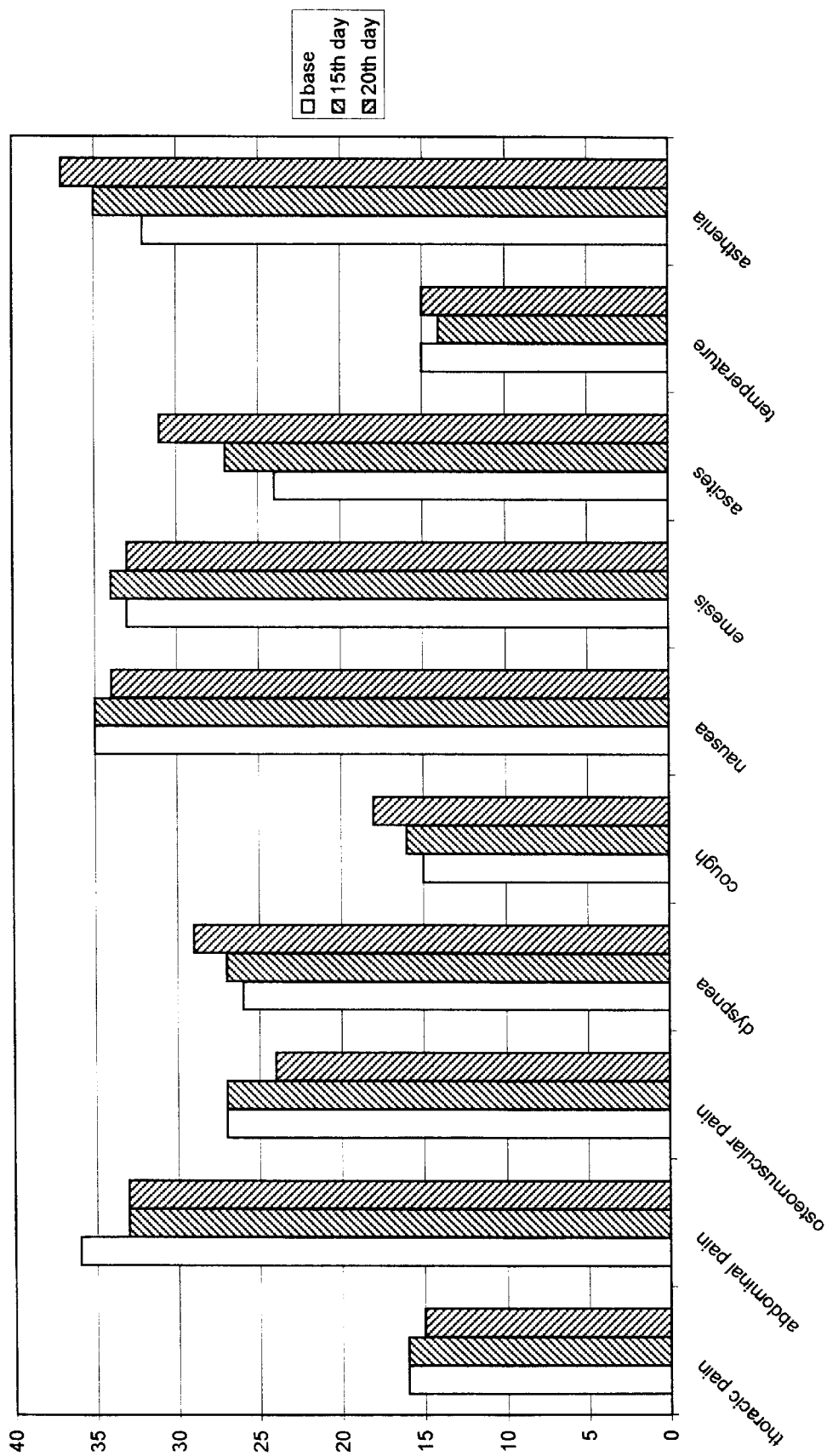
FIG. 7 is a graph showing the change in symptoms among patients treated with a second compound different from the alimentary integrator of the present invention.

The graph of FIG. 6 is relevant to the changes in symptoms among 4 patients treated using potassium citrate, while the graph of FIG. 7 is relevant to the changes in symptoms among 4 patients treated using potassium tartarate. Similarly to the graph of FIG. 5, on abscissa each graph presents the different symptoms; from left to right-thoracic pain, abdominal pain, osteomuscular pain-dyspnea, cough, nausea, emesis, ascites, temperature, asthenia. The columns are composed by three secondary columns which refer to the different time of recording of the data, with 10 days interval; from left to right base condition (at the beginning of the treatment), at 10th day and at 20th day. Also in these cases the rate utilized as ordinate in the graph is relevant to the intensity (amount) of the symptoms. With both the comparison compounds the symptoms have had a not positive progress with a substantially increasing symptoms rate.

What is claimed is:

1. An alimentary integrator which consists essentially of a compound formed from potassium bicarbonate and ribose.

2. An alimentary integrator which consists of potassium ribosate.

3. An alimentary integrator which consists essentially of a compound formed from potassium bicarbonate, ribose and l-ascorbic acid.

4. An alimentary integrator which consists of potassium ribose ascorbate.

5. An alimentary integrator which consists essentially of a compound selected from the group consisting of potassium ribosate and potassium ribose ascorbate.

6. The integrator of claim 5 wherein the potassium ribose is formed from two to four parts by weight of . potassium bicarbonate and one part by weight of ribose, and the potassium ribosate ascorbate is formed from two or four parts by weight of potassium bicarbonate, one part by weight of l-ascorbic acid and an amount of ribose corresponding to 0.1–10% by weight of the sum of the weights of the potassium bicarbonate and l-ascorbic acid.

7. An alimentary integrator which consists of a compound selected from the group consisting of potassium ribosate and potassium ribose ascorbate.

8. A method of treating a potassium deficiency based disease or condition in a subject involving neoplasia, comprising administering to the subject an effective amount of an alimentary integrator which consists essentially of a compound formed from potassium bicarbonate and ribose.

9. A method of treating a potassium deficiency based disease or condition in a subject involving neoplasia, comprising administering to the subject an effective amount of an alimentary integrator which consists of a compound formed from potassium bicarbonate and ribose.

10. A method of treating a potassium deficiency based disease or condition in a subject involving neoplasia, comprising administering to the subject an effective amount of an alimentary integrator which consists essentially of a compound formed from potassium bicarbonate, ribose and l-ascorbic acid.

11. A method of treating a potassium deficiency based disease or condition in a subject involving neoplasia, comprising administering to the subject an effective amount of an alimentary integrator which consists of a compound formed from potassium bicarbonate, ribose and l-ascorbic acid.

12. A method of treating a potassium deficiency based disease or condition in a subject involving neoplasia, comprising administering to the subject an effective amount of an alimentary integrator which consists essentially of a compound selected from the group consisting of potassium ribosate and potassium ribose ascorbate.

13. The method of claim 12 wherein the potassium ribosate is formed from two to four parts by weight of potassium bicarbonate and one part by weight of ribose, and the potassium ribose ascorbate is formed from two or four parts by weight of potassium bicarbonate, one part by weight of l-ascorbic acid and an amount of ribose corresponding to 0.1–10% by weight of the sum of the weights of the potassium bicarbonate and l-ascorbic acid.

* * * * *